United States Patent [19]

Santilli et al.

[11] 4,148,801
[45] Apr. 10, 1979

[54] 3-[(CHLOROPHENYLSULFONYL)METHYL]-1,2,4-OXADIAZOLE-5-CARBOXYLIC ACID DERIVATIVES

[75] Inventors: Arthur A. Santilli, Havertown; Robert L. Morris, Devon, both of Pa.

[73] Assignee: American Home Products Corporation, New York, N.Y.

[21] Appl. No.: 921,293

[22] Filed: Jul. 3, 1978

[51] Int. Cl.² .................................. C07D 271/06
[52] U.S. Cl. .................... 260/307 G; 260/465 G; 260/564 G; 424/272
[58] Field of Search .................... 260/307 G

[56]  References Cited

U.S. PATENT DOCUMENTS 2,897,079   7/1959   DeCat et al. .................... 96/55
3,755,306   8/1973   Treuner .................... 260/239.9

OTHER PUBLICATIONS

Palazzo et al., Gazz. Chim. Ital., 90, 1290–1298, (1970).
Behr-Chapter IX, "1,2,4-Oxadiazoles," *The Chemistry of Heterocyclic Compounds*, 17, 252–253, (1962).
Treuner, *Synthesis*, 559–560, (Oct. 1972).
Clapp–"1,2,4-Oxadiazoles," *Advances to Heterocyclic Chemistry*, 20, 97–99.

*Primary Examiner*—Raymond V. Rush
*Attorney, Agent, or Firm*—Arthur G. Seifert

[57]  ABSTRACT

Disclosed herein are 3-[(chlorophenylsulfonyl)methyl]-1,2,4-oxadiazole-5-carboxylic acid derivatives and 3-[(chlorophenylsulfonyl)ethyl]-1,2,4-oxadiazole-5-carboxylic acid derivatives exhibiting antihypertensive or antiviral activity and having the following formula:

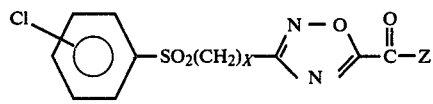

wherein:
X = 1 or 2; and
Z is —OR, —OH, —OK, —ONa, —NHOH, —NHNH₂, —NHNHCOCO₂R, or —NHNHSO₂R; and
R is —CH₃, —CH₂CH₃, —CH₂CH₂CH₃ or —CH(CH₃)₂.

11 Claims, No Drawings

3-[(CHLOROPHENYLSULFONYL)METHYL]-1,2,4-OXADIAZOLE-5-CARBOXYLIC ACID DERIVATIVES

BACKGROUND OF THE INVENTION

This invention relates to 1,2,4-oxadiazole compounds substituted in the 3-position with a (chlorophenylsulfonyl)methyl or chlorophenylsulfonyl)ethyl group and variously substituted in the 5-position with carboxylic acid derivatives, such as carboxylic acid salts, esters, or hydrazine derivatives; and the pharmacologically acceptable acid addition salts of such compounds which have a bsic nitrogen moiety. Except where Z is $NHNH_2$, said compounds exhibit antihypertensive activity in standard pharmacological tests in animals; compounds where Z is —$NHNH_2$ exhibit antiviral activity against influenza B Mass. virus.

SUMMARY OF THE INVENTION

The compounds of the present invention are represented by the Formula I:

[Formula I: Cl-phenyl-$SO_2(CH_2)_x$-oxadiazole-C(=O)-Z]

wherein:
X = 1 or 2; and
Z is —OR, —OH, —OK, —ONa, —NHOH, —$NHNH_2$, —$NHNHCOCO_2R$, or —$NHNHSO_2R$; and
R is —$CH_3$, —$CH_2CH_3$, —$CH_2CH_2CH_3$, or —$CH(CH_3)_2$.

A particularly preferred group of said compounds are those in which the chlorine substituent is in the 4-position on the phenyl ring.

Another preferred group of compounds are those in which Z is —OR, —OH, —OK, or —ONa.

Yet another preferred group of compounds are those in which Z is —NHOH, —$NHNH_2$, —$NHNHCOCO_2R$, or —$NHNHSO_2R$. Such compounds wherein X=1 are particularly preferred.

Included in the present invention are the pharmacologically acceptable acid addition salts of the compounds of Formula I which contain a basic nitrogen moiety. When used herein the term "alkyl" (such as "alkyl ester" or "alkylsulfonyl") is coextensive with the definition of R given above, namely —$CH_3$, —$CH_2CH_3$, —$CH_2CH_2CH_3$ and —$CH(CH_3)_2$ (i.e. the methyl, ethyl, propyl, and isopropyl groups). The —$CH_3$ and —$CH_2CH_3$ groups are preferred R ("alkyl") substituents.

At times herein the compounds of the invention will be referred to in terms of the particular 5-carboxylic acid derivatives. For example a reference to "the 5-carboxylic acid unsubstituted hydrazides of the invention" refers to those compounds of the invention described in Formula I in which Z is —$NHNH_2$, X may be 1 or 2, and the chlorine atom may be at the 2, 3, or 4-position on the phenyl ring of the 3-(chlorophenylsulfonyl)-methyl [or ethyl] moiety.

The compounds of Formula I exhibit anti-hypertensive activity in standard pharmacological tests in animals, except where Z is —$NHNH_2$. The 5-carboxylic acid unsubstituted hydrazides are useful as intermediates for the preparation of th 5-carboxylic acid 2-(alkylsulfonyl)hydrazides and 5-carboxylic acid 2-(ethoxyoxalyl)hydrazides of the invention. Additionally, the 5-carboxylic acid unsubstituted hydrazides of the invention exhibit in vivo antiviral activity against influenza B Mass virus.

DETAILED DESCRIPTION OF THE INVENTION

The 3-[(chlorophenylsulfonyl)methyl]-1,2,4-oxadizaole-5-carboxylic acid esters (Ia, X=1) of the present invention are formed by treating the appropriate 2-(chlorophenylsulfonyl)-N-hydroxyethanimidamide (III) with a lower alkyl oxalyl chloride as shown below:

[Reaction: (III) Cl-phenyl-$SO_2(CH_2)_x$-C(=NOH)$NH_2$ + $ClCOCO_2R$ → (Ia) Cl-phenyl-$SO_2(CH_2)_x$-C(=N-O-)=C(N)-$CO_2R$]

This reaction may be conveniently carried out using tetrahydrofuran as a solvent under reflux conditions. If it is desired to make a 1,2,4-oxadizaole of the invention having a (chlorophenylsulfonyl)ethyl group (ie. X=2) at the 3-position, then the starting imidamide (III) would be the appropriate 3-(chlorophenylsulfonyl)N-hydroxypropanimidamide. The appropriate imidamide has the chlorine in the same position on the phenyl ring as desired in the 1,2,4-oxadiazole end product.

The 2-chlorophenylsulfonyl-N-hydroxyethanimidamides (III, X=1) or 3-chlorophenylsulfonyl-N-hydroxypropanimidamides (III, X=2) are preferrably produced by treating the appropriate chlorophenylsulfonylacetonitrile (II, X=1) or chlorophenylsulfonylpropionitrile (II, X=2) with hydroxylamine hydrochloride in the presence of a mild base such as sodium carbonate. The general reaction is shown below and may be carried out in solutions of ethanol and water at room temperature.

[Reaction: (II) Cl-phenyl-$SO_2(CH_2)_xCN$ + $NH_2OH \cdot HCl$ + $Na_2CO_3$ → (III) Cl-phenyl-$SO_2(CH_2)_x$-C(=NOH)$NH_2$]

Such chlorophenylsulfonylacetonitriles or chlorophenylsulfonylpropionitrates, are available commercially or are readily produced from readily available starting materials by known chemical reactions.

In order to obtain the potassium or sodium salt of the product 1,2,4-oxadiazoles (ia) described above, the 5-carboxylic acid alkyl ester (obtained from the above-described sequence of reactions) may be treated with a solution of potassium hydroxide or sodium hydroxide in methanol (or ethanol) under reflux. The 5-carboxylic acids of the subject 1,2,4-oxadiazoles may conveniently be obtained from said lower alkyl esters by treating the ester with an acid solution, preferably hydrochlorice acid in methanol.

The 5-(N-hydroxy)carboxamides (Ib) of the present invention may be produced by treating the 5-carboxylic acid alkyl esters (preferrably the ethyl esters) with hydroxylamine. These reactions may conveniently be carried out at room temperature using methanol as a solvent.

The 5-carboxylic acid esters of the invention also serve as intermediates for the production of the 5-carboxylic acid unsubstituted hydrazides (Ic) of the invention. These unsubstituted hydrazides are usually formed by treating the 5-carboxylic acid ester (preferrably the ethyl ester) with hydrazine in a solvent such as ethanol. The reaction is usually carried out first under cooling conditions and then at room temperatures.

Similarly, the 5-carboxylic acid unsubstituted hydrazides of the invention serve as intermediates in the production of the 5-carboxylic acid 2-(alkylsulfonyl)hydrazides (Id) and in the production of the 5-carboxylic acid 2-(ethoxyoxalyl)hydrazides (Ie). Treating the 5-carboxylic acid unsubstituted hydrazides with an alkyl sulfonyl chloride usually at room temperature in a pyridine reaction solution produces the subject 5-carboxylic acid 2-(alkylsulfonyl)hydrazides (Id). Treating the 5-carboxylic acid unsubstituted hydrazides with an alkyl oxalyl chloride, usually under reflux heating in a tetrahydrofuran reaction solution, produces the subject 5-carboxylic acid 2-(ethoxyoxalyl)hydrazides (Ie).

The reaction sequence described above for the production of the 5-(N-hydroxy)carboxamides (Ib), the 5-carboxylic acid hydrazides (Ic) and the derivatives of the hydrazides (Id & Ie) is illustrated below:

drochloric, hydrobromic, sulfonic, sulfuric, phosphoric, nitric, maleic, fumaric, benzoic, ascorbic, pamoic, succinic, methanesulfonic, acetic, proprionic, tartaric, citric, lactic, malic, mandelic, cinnamic, palmitic, itaconic, and benzenesulfonic. Such salts are included in the scope of the invention.

Compounds of the invention exhibit anti-hypertensive effects in warm-blooded animals as evidenced by standard pharmacological tests in animals. The anti-hypertensive activity of the compounds can be demonstrated by following a test procedure using unanesthetized rats. In the procedure systolic pressure of male spontaneously hypertensive rats is measured by an indirect technique using the Decker Caudal Plethysmograph or other appropriate sensor. Test groups usually consist of four such rats and the test and standard compounds (drugs) are usually administered orally. Blood pressures are usually read prior to drug administration and at 1.5, 4 and 24 hours thereafter. A standard compound may be chosen from clonidine, hydralazine, guanethidine, methyldopa, or resperpine.

The compounds of the invention (except for the 5-carboxylic acid hydrazides) decrease the blood pressure when administered according to this test procedure at doses of 75 mg. per kilogram of body weight (mg/kg) or less.

When used to treat hypertension in warm-blooded animals the effective dosage of the compound of the invention will depend upon the stage and severity of the condition being treated, the subject being treated, and the particular compound being used, and will readily be determined by the attending physician. Therapy should be initiated at lower dosages, usually 10 mg/kg per day or less, the dosage thereafter being increased, if neces-

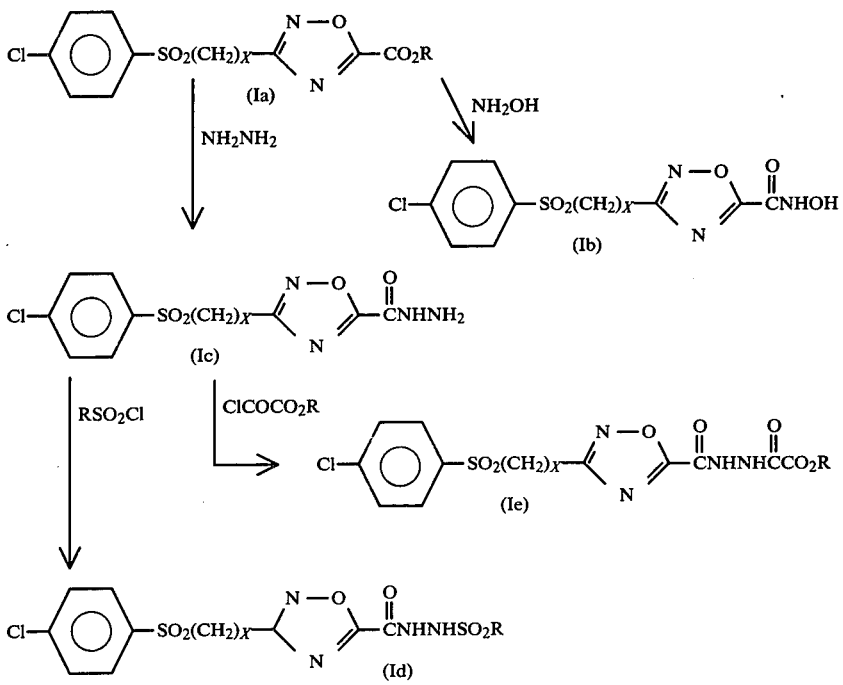

For pharmacological use, those compounds of Formula I which contain a basic nitrogen moiety may be administered in the form of an acid addition salt of a non-toxic organic or inorganic acid. Such salts may be prepared by methods well-known in the art. Appropriate salts may be formed from the following acids: hysary, until the desired anti-hypertensive effect is obtained.

Other compounds of the invention exhibit in vivo antiviral activity against influenza B Mass. virus. The antiviral activity of the compounds can be demonstrated by following a test procedure using 12–14 gram mice. Ten such mice are treated with each dilution of a test compound 24 hours prior to and at 1, 24, 48, and 72 hours after inoculation with a standardized challenge dose of the test virus. The mice are inoculated intraperitoneally with the test compound and intranasally with the ifluenza virus. Twenty mice inoculated with saline instead of the test compound serve as the control group. All the mice are observed for 21 days and the number of deaths occurring in each group are recorded. Antiviral activity of a test compound is scored statistically for significance at the 95 and 99% confidence levels on the basis of percentage of survivals and prolongation of life.

The following examples further illustrate the best mode contemplated by the inventors for the practice of the invention.

EXAMPLE 1

2-(4-Chlorophenylsulfonyl)-N-Hydroxyethanimidamide 50 g. (0.23 mole) of 4-chlorophenylsulfonylacetonitrile were dissolved in 1.5 liters of ethanol and 16 g. (0.23 mole) of hydroxylamine HCl in 150 ml. of water was added to this solution, followed by the addition of 14.4 g. (0.12 mole) of $Na_2CO_3$ in 150 ml. of water. This reaction mixture was stirred at room temperature overnight. 58 g. crude product were filtered off; this was recrystallized from about 2.5 liters of ethanol to give 40 g. of the product (70% yield).

Analysis for: $C_8H_9ClN_2O_3S$— Calculated: C, 38.65; H, 3.65; N, 11.27; Cl, 14.26; S, 12.90, Found: C, 38.53; H, 3.65; N, 11.28; Cl, 14.22; S, 12.63.

EXAMPLE 2

3-(4-Chlorophenylsulfonyl)-N-hydroxypropanimidamide 17.8 g. (.078 moles) of 4-chlorophenylsulfonyl proprionitrile was dissolved in 200 ml. of ethanol and, to this was added 5.4 g. (0.078 moles) of hydroxylamine HCl in 25 ml. of water, followed by 4.7 g. (0.04 moles) of $Na_2CO_3$ in 25 ml. of water. This reaction mixture was stirred at room temperature for 1.5 hours and then the crude product was filtered off and recrystallized from 95% ethanol to give 6 g. of material, m.p. 205° (dec.).

Analysis for: $C_9H_{11}ClN_2O_3S$— Calculated: C, 41.15; H, 3.84; N, 10.67. Found: C, 41.15; H, 4.04; N, 10.67.

EXAMPLE 3

3-[(4-Chlorophenylsulfonyl)Methyl]-1,2,4-Oxadiazole-5-Carboxylic Acid Ethyl Ester To a solution of 10 g. (.04 mole) of 2-(4-chlorophenylsulfonyl)-N-hydroxyethanimidamide in tetrahydrofuran was added 5.48 g. (0.04 mole) of ethyl oxalyl chloride in tetrahydrofuran and this reaction mixture was refluxed for 2½ hours, then stripped to dryness on a rotary evaporator. The crude product was recrystallized from 95% ethanol to give 10 g. of the product as white needles, m.p. 181–184° C (dec.).

Analysis for: $C_{12}H_{11}ClN_2O_5S$— Calculated: C, 43.57; H, 3.35; N, 8.47. Found: C, 43.55; H, 3.10; N, 848.

EXAMPLE 4

3-[(4-Chlorophenylsulfonyl)Methyl]-1,2,4-Oxadiazole-5-Carboxylic Acid Potassium Salt, Hydrate 2 g. of 85% KOH (0.03 mole) were dissolved in methanol and then 5.g (0.015 mole) of 3-[(4-chlorophenylsulfonyl)methyl]-1,2,4-oxadiazole, 5-carboxylic acid ethyl ester were added to this solution. The resulting reaction mixture was refluxed for 3 hours. The product was filtered off and recrystallized from ethanol to give 1.7 g. of clean product, m.p. 187° C (dec.), as the monohydrate.

Analysis for: $C_{10}H_8ClN_2KSO_6$— Calculated: C, 33.47; H, 2.24; N, 7.81. Found: C, 33.09; H, 2.11; N, 7.72.

EXAMPLE 5

3-[2-(4-Chlorophenylsulfonyl)Ethyl]-1,2,4-Oxadiazole-5-Carboxylic Acid Ethyl Ester 4.85 g. (.019 mole) of 3-(4-chlorophenylsulfonyl)-N-hydroxypropanimidamide were added to THF and to this mixture 2.52 g. (0.019 mole) of ethyl oxalyl chloride also in THF were added. The resulting reaction mixture was then refluxed 2½ hours. The white solid precipitate was filtered off and the filtrate stripped on an evaporator. Ether was added to this residue and the solid that formed was recrystallized from ethanol to give 1.5 g. of the product, m.p. 115–119° C.

Analysis for: $C_{13}H_{13}ClN_2O_5S$— Calculated: C, 45.29; H, 3.79; N, 8.12. Found: C, 45.28; H, 3.85; N, 8.13.

EXAMPLE 6

3-[(4-Chlorophenylsulfonyl)Methyl]-1,2,4-Oxadiazole-5-(N-hydroxy)Carboxamide

The free base of hydroxylamine hydrochloride was prepared by adding 0.66 g. (0.017 mole) of NaOH to 1.26 g. (0.018 mole) $NH_2OH\cdot HCl$ in MeOH (slightly basic solution) and then this was added to 3.0 g. (.0009 mole) of 3-[(4-chlorophenylsulfonyl)-methyl]-1,2,4-oxadiazole, 5-carboxylic acid ethyl ester in methanol. This reaction mixture was stirred 4 days at room temperature. The reaction mixture was then stripped to dryness and the residue recrystallized several times from water to give 1.3 g. of the product, m.p. 160° C. (dec.).

Analysis for: $C_{10}H_8ClN_3O_5S$— Calculated: C, 37.80; H, 2.54; N, 13.23. Found: C, 37.97; H, 2.41; H, 13.42.

EXAMPLE 7

3-[(4-Chlorophenylsulfonyl)Methyl]-1,2,4-Oxadiazole-5-Carboxylic Acid Hydrazide

Five ml. of 95% hydrazine (.15 moles) in ethanol was added slowly, with stirring, to 3-[(4-chlorophenylsulfonyl)methyl]-1, 2,4-oxadiazole, 5-carboxylic acid ethyl ester suspended in ethanol at 5° C. This reaction mixture was stirred in ice for 5 hours and then overnight at room temperature. The product was filtered off and recrystallized from ethanol to give 8 g. of the product, with m.p. 177° C.

Analysis for: $C_{10}H_9ClN_4O_4S$— Calculated: C, 37.92; H, 2.86; N, 17.69. Found: C, 37.92; H, 2.85; N, 17.96.

EXAMPLE 8

3-[(4-Chlorophenylsulfonyl)Methyl]-1,2,4-Oxadiazole-5-Carboxylic Acid 2-(Methylsulfonyl)hydrazide 5.0 g. (0.016 mole) of 3-[(4-chlorophenylsulfonyl)methyl]-1,2,4-oxadiazole, 5-carboxylic acid hydrazide were dissolved in pyridine and 1.8 g. (0.016 mole) of methane sulfonyl chloride were added to this solution. This reaction mixture was stirred at room temperature for 3½ hours, then added to water, neutralized with concentrated HCl, and chilled. The solid product was collected and recrystallized from acetonitrile to give 1.2 g. of the product, m.p. 198–202° C.

Analysis for: $C_{11}H_{11}ClN_4O_6S$— Calculated: C, 33.46; H, 2.81; N, 14.19. Found: C, 33.88; H, 3.03; N, 14.64.

EXAMPLE 9

3-[(4-Chlorophenylsulfonyl)Methyl]-1,2,4-Oxadiazole-5-Carboxylic Acid 2-(Ethoxyoxalyl)hydrazide 4.0 g. (.013 mole) of 3-[(4-chlorophenylsulfonyl)-methyl]-1,2,4-oxadizole, 5-carboxylic acid hydrazide were dissolved in THF and to this were added 1.72 g. (.013 mole) of ethyl oxalyl chloride in THF, this reaction mixture was refluxed for 1 hour. The reaction mixture was thereafter stripped to dryness, and the solid residue was reprecipitated from chloroform and pet ether and then recrystallized from ethanol to give 3.5 g. of the product, m.p. 161–164° C.

Analysis for: $C_{14}H_{13}ClN_4O_7S$— Calculated: C, 40.34; H, 3.14; N, 13.44; Cl, 8.51; S, 7.69. Found: C, 40.37; H, 2.99; N, 13.53; Cl, 8.43; S, 7.70.

What is claimed is:

1. A compound represented by the formula:

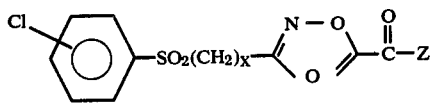

wherein
X = 1 or 2;
Z is —OR, —OH, —OK, —ONa, —NHOH, —NHNH$_2$, —NHNHCOCO$_2$R, or —NHNHSO$_2$R; and
R is —CH$_3$, —CH$_2$CH$_3$, —CH$_2$CH$_2$CH$_3$ or —CH(CH$_3$)$_2$.

2. A compound represented by the formula:

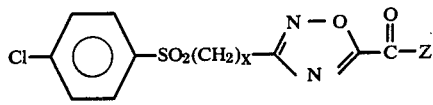

wherein
X = 1 or 2; and
Z is —OR, —OH, —OK, —ONa, —NHOH, —NHNH$_2$, —NHNHCOCO$_2$R, or —NHNHSO$_2$R; and
R is —CH$_3$, —CH$_2$CH$_3$, —CH$_2$CH$_2$CH$_3$ or —CH(CH$_3$)$_2$.

3. A compound of claim 2 wherein R is —CH$_3$ or —CH$_2$CH$_3$.

4. A compound of claim 3 wherein X = 1.

5. A compound of claim 2 wherein X = 1, Z is —OR, and R is —CH$_2$CH$_3$, said compound being 3-[(4-chlorophenylsulfonyl)methyl]-1,2,4-oxadiazole-5-carboxylic acid ethyl ester.

6. A compound of claim 2 wherein X = 2, Z is —OR and R is —CH$_2$CH$_3$, said compound being 3-[2-(4-chlorophenylsulfonyl)ethyl]-1,2,4-oxadiazole-5-carboxylic acid ethyl ester.

7. A compound of claim 2 wherein X = 1, and Z is —OK, said compound being 3-[(4-chlorophenylsulfonyl)methyl]-1,2,4-oxadiazole-5-carboxylic acid potassium salt.

8. A compound of claim 2 wherein X = 1, and Z is —NHOH, said compound being 3-[(4-chlorophenylsulfonyl)methyl]-1,2,4-oxadiazole-5-(N-hydroxy)carboxamide.

9. A compound of claim 2 wherein X = 1, and Z is -NHNH$_2$, said compound being 3-[(4-chlorophenylsulfonyl)methyl]-1,2,4-oxadiazole-5-carboxylic acid hydrazide.

10. A compound of claim 2 wherein X = 1, and Z is NHNHSO$_2$R, and R is CH$_3$, said compound being 3-[(4-chlorophenylsulfonyl)methyl]-1,2,4-oxadiazole-5-carboxylic acid 2-(methylsulfonyl)hydrazide.

11. A compound of claim 2 wherein X = 1, and Z is NHNHCOCO$_2$R, and R is —CH$_2$CH$_3$, said compound being 3-[(4-chlorophenylsulfonyl)methyl]-1,2,4-oxadiazole-5-carboxylic acid (2-ethoxyoxalyl)hydrazide.

* * * * *